US006860866B1

(12) United States Patent
Graf et al.

(10) Patent No.: US 6,860,866 B1
(45) Date of Patent: Mar. 1, 2005

(54) METHOD OF DETERMINING THE EFFICIENCY OF A DIALYZER OF A DIALYSIS MACHINE AND A DIALYSIS MACHINE FOR CARRYING OUT THIS METHOD

(75) Inventors: Thomas Graf, Kuetzberg (DE); Christoph Bardorz, Rottendorf (DE); Malte Gross, Niedewerrn (DE); Rainer Goldau, Kastorf (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 178 days.

(21) Appl. No.: 09/599,334

(22) Filed: Jun. 22, 2000

(30) Foreign Application Priority Data

Jun. 22, 1999 (DE) .......................... 199 28 407

(51) Int. Cl.[7] ................. A61M 37/00; B01D 63/00; B01D 35/00; C02F 1/44; A61B 5/00
(52) U.S. Cl. ............. 604/5.01; 210/645; 210/646; 210/85; 210/321.71; 210/739; 210/257.2; 600/366
(58) Field of Search .................. 600/366; 604/4.01, 604/5.01, 5.02–5.04, 6.09, 19, 27, 28; 422/44; 210/645–47, 650–51, 739, 745, 85, 87, 90, 194, 195.1, 196, 195.2, 252, 257.1–257.2, 258, 321.6, 321.65, 321.71, 321.72–321.78, 321.84, 348, 416.1, 500.1, 500.21

(56) References Cited

U.S. PATENT DOCUMENTS 5,744,031 A * 4/1998 Bene .................. 210/321.71
6,187,199 B1 * 2/2001 Goldau ................. 210/646
6,258,027 B1 * 7/2001 Sternby ................ 600/366

FOREIGN PATENT DOCUMENTS

| DE | 39 38 662 | 7/1991 |
|----|-----------|--------|
| DE | 42 39 937 | 8/1995 |
| DE | 197 39 100 | 4/1999 |

OTHER PUBLICATIONS

Hans Eduard Franz, "Blutreinigungsverfahren (Blood Purification Method)", Georg Thieme Verlag Suttgart, New York 1990, pp. 11–13.

Jan Erik Sigdell et al., "Clearance of a Dialyzer Under Varying Operating Conditions", Artificial Organs, 1986, pp. 219–225.

* cited by examiner

Primary Examiner—Patricia Bianco
(74) Attorney, Agent, or Firm—Kenyon & Kenyon

(57) ABSTRACT

A method and a device for determining the efficiency of a dialyzer of a dialysis machine during a dialysis treatment wherein the dialyzer is divided by a semipermeable membrane into a blood chamber and a dialysis fluid chamber and wherein the blood flows at a predetermined flow rate through the blood chamber and dialysis fluid flows at a predetermined flow rate through the dialysis fluid chamber. In use, the dialysance or clearance for a predetermined dialysis fluid flow rate and/or blood flow rate is measured, and then the dialysance or clearance for any dialysis fluid flow rate and blood flow rate is calculated.

6 Claims, 1 Drawing Sheet

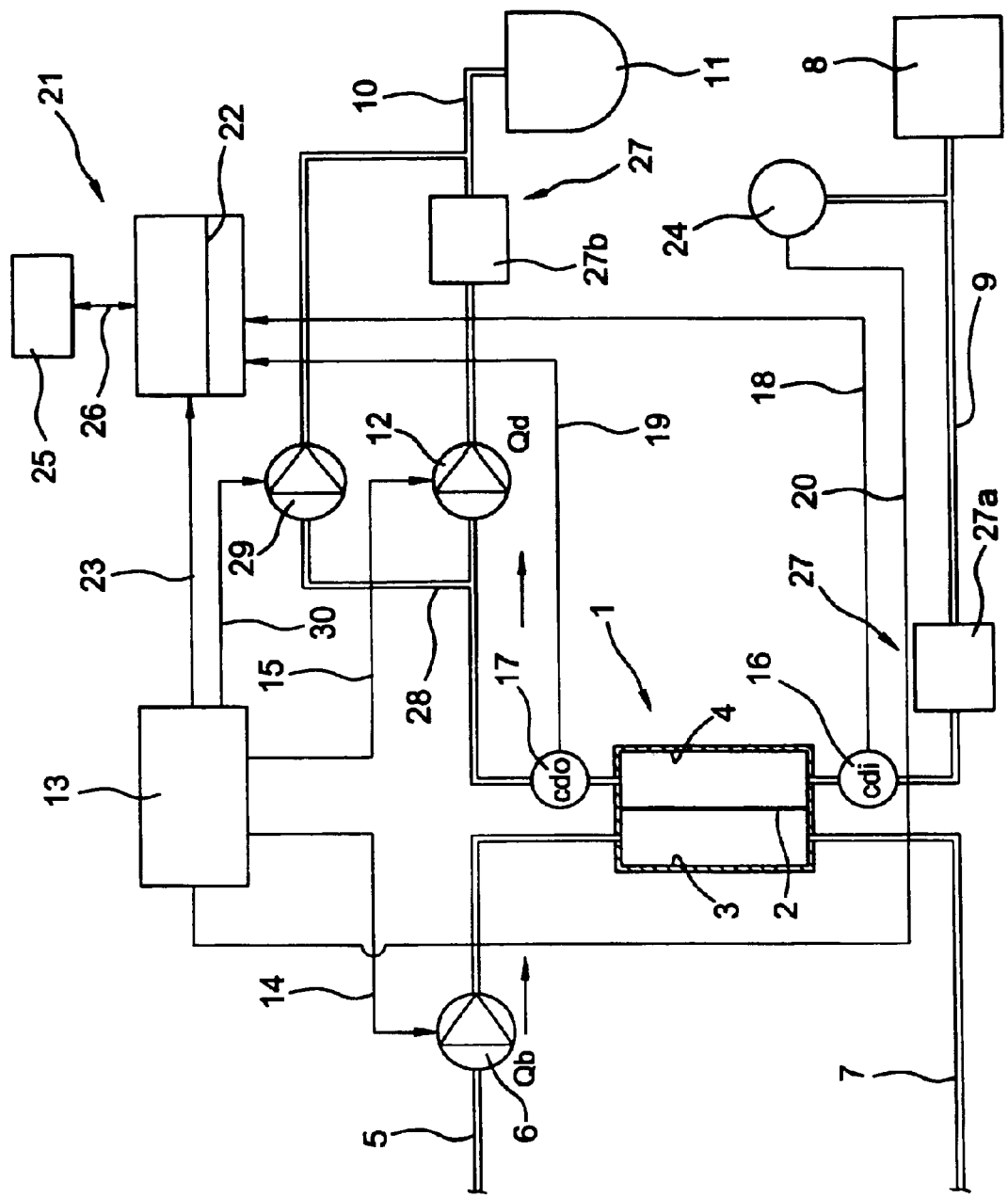

METHOD OF DETERMINING THE EFFICIENCY OF A DIALYZER OF A DIALYSIS MACHINE AND A DIALYSIS MACHINE FOR CARRYING OUT THIS METHOD

FIELD OF THE INVENTION

The present invention relates to a method of determining the efficiency of a dialyzer of a dialysis machine during a dialysis treatment wherein the dialyzer is divided by a semipermeable membrane into a blood chamber and a dialysis fluid chamber and wherein blood flows at a predetermined flow ii rate through the blood chamber and dialysis fluid flows at a predetermined flow rate through the dialysis fluid chamber. In addition, the present invention relates to a dialysis machine for carrying out this method.

BACKGROUND OF THE INVENTION

Mass exchange in the dialyzer has both a convective component and a diffusive component. In diffusive mass exchange, the mass transfer per unit of time for the respective substance through the membrane is proportional to the concentration gradient between the blood and the dialysis fluid. In convective mass transport, the mass transfer depends on the quantity of filtrate, because the concentration of filterable substances is the same in both the blood and the filtrate. See, Hans Eduard Franz, *Blutreinigungsverfahren* [*Blood Purification Method*], pp. 11–13 (Georg Thieme Verlag Stuttgart, New York 1990).

Since the concentration gradient is reduced continuously during a dialysis treatment, no fixed numerical value can be given for the quantity of substance exchanged per unit of time. Clearance is a measured quantity for the efficiency of a dialyzer and is independent of the concentration. The clearance of a substance is the component of the total flow through the dialyzer which has been freed completely of the substance in question.

Dialysance is another term for determining the efficiency of a dialyzer, with the concentration of the substance in the dialysis fluid also being taken into account.

The following is obtained for determination of the dialysance, D, or clearance, K, for a given substance such as sodium.

Dialysance D is equal to the ratio of the mass transport of the respective substance Qb (cbi–cbo) on the blood side, to the difference between the concentrations of the substance in the blood and the dialysis fluid at the respective inlets of the dialyzer (cbi–cdi).

$$D = Qe \frac{(cbi - cbo)}{cbi - cdi} \quad (1)$$

For mass balance reasons, it holds that:

$$Qe \cdot (cbi - cbo) = -Qd \cdot (cdi - cdo) \quad (2)$$

It follows from (1) and (2) for the dialysance on the dialysate side:

$$D = -Qd \frac{(cdi - cdo)}{cbi - cdi} \quad (3)$$

where in equations (1) through (3):

Qe = effective blood flow;
Qd = dialysis fluid flow rate;
cb = concentration of the substance in the solution volume of the blood;
cd = concentration of the substance in the dialysis fluid;
i = inlet of the dialyzer; and
o = outlet of the dialyzer.

The effective blood flow is the flow of the blood component in which the substances participating in the dialyzer metabolism are dissolved, i.e., it is based on the complete (aqueous) solution volume for the respective substance. This may be the plasma water flow or the blood water flow, depending on the substance.

For the case of a specific metabolic excretion product such as urea, cdi is zero, because this substance should not be present in the fresh dialysis fluid when properly used. Otherwise, one would no longer speak of the dialysance D of this substance, but rather the clearance C of this metabolic product.

German Patent No. 39 38 662 describes a method of in vivo determination of parameters of hemodialysis, in particular of the dialysance, where the dialysate-electrolyte transfer is measured at two different inlet dialysate concentrations. On the assumption that the blood inlet concentration is constant, the dialysance is determined according to the known method by determining the difference between the differences in the dialysis fluid ion concentration at the inlet and outlet sides of the dialyzer at the time of the first and second measurements, dividing this by the difference between the dialysis fluid ion concentration at the inlet side at the time of the first and second measurements, and multiplying this by the dialysis fluid flow rate.

In this method, the relatively long measurement time has proven to be a disadvantage for monitoring the course of dialysance over time during the dialysis treatment. This long measurement time is due to the fact that after the new inlet concentration of the dialysis fluid is set, a steady state must first be established at the outlet of the dialyzer before the measured value can be recorded. As a result, a certain period of time must elapse before a jump in conductivity at the dialyzer inlet leads to stable conditions at the dialyzer outlet.

German Patent No. 197 39 100 describes a method of determining the maximum dialysance during a dialysis treatment. In this method, the dialysis fluid inlet concentration of a certain substance in the dialysis fluid is determined upstream from the dialysis fluid chamber of the dialyzer, the outlet concentration of the respective substance in the dialysis fluid is determined downstream from the dialysis fluid chamber, and the inlet concentration of the substance in the blood stream is determined upstream from the blood chamber of the dialyzer. The maximum dialysance is determined from the dialysis fluid inlet and outlet concentrations, the blood inlet concentration, the blood flow through the blood chamber and the dialysis fluid flow rate through the dialysis fluid chamber. One disadvantage of this method is that it allows a determination of only the maximum dialysance, but not of the dialysance for any desired dialysis fluid or blood flow rate.

SUMMARY OF THE INVENTION

The object of the present invention is to provide a method which makes it possible to easily monitor the efficiency of a dialyzer during a dialysis treatment without any delay and to create a dialysis machine which permits simple monitoring of the efficiency of the dialyzer without any delay.

In use, the dialysance and/or clearance of the dialyzer for any given dialysis fluid rate, blood flow rate and/or ultrafiltration rate is determined on the basis of the clearance and/or dialysance established at a preselected dialysis fluid rate, blood flow rate and/or ultrafiltration rate, where the clearance and/or dialysance established at the predetermined dialysis fluid rate, blood flow rate and/or ultrafiltration rate can be measured in a known manner during the dialysis treatment. To this extent, only a single measurement is necessary to be able to monitor the course of the clearance and/or dialysance over time.

If the clearance and/or dialysance established at the given dialysis fluid rate, blood flow rate or ultrafiltration rate is known, it need not be measured. For example, the efficiency of the dialyzer for any desired dialysis fluid rate, blood flow rate or ultrafiltration rate can be determined on the basis of the clearance and/or dialysance of the dialyzer given by the manufacturer for a given dialysis fluid rate, blood flow rate or ultrafiltration rate.

Essentially, the clearance and/or dialysance can be estimated throughout the course of the entire dialysis treatment on the basis of the clearance and/or dialysance established at a given dialysis fluid rate, blood flow rate or ultrafiltration rate. To enhance accuracy, the entire dialysis treatment can also be divided into individual time segments in which the monitoring is then performed on the basis of one measurement per individual time segment.

To monitor the efficiency of the dialyzer, the clearance and/or dialysance can be determined continuously as a function of the dialysis fluid rate, blood flow rate or ultrafiltration rate during the dialysis treatment. The effective clearance and/or dialysance can then be determined by averaging.

The dialysis fluid rate, blood flow rate or ultrafiltration rate can be measured during the dialysis treatment. In addition, the delivery rates of the blood pump and/or the dialysis fluid pump can be detected in the arterial or venous blood line, the dialysis fluid inlet line, and/or the dialysis fluid outlet line for determination of the flow rates. The ultrafiltration rate is obtained by measuring the difference between the flows in the inlet and outlet lines; it can also be predetermined by the delivery rate of an ultrafiltration pump, as described in German Patent No. 42 39 937, for example.

The device for determining the clearance and/or dialysance of the dialysis machine has a computer unit in which the corresponding parameters of dialysis are calculated.

The method and/or device according to the present invention can be used to particular advantage in cases where the flow rates change automatically because of instrument drift without the user effecting any direct change in flow.

In addition, a hemodialysis treatment necessarily leads to a change in the composition of the blood during the treatment. The aqueous component in particular is reduced by ultrafiltration, which generally causes a change in the effective blood flow, Qe, and the hematocrit without any external change in the pumping rate of the blood pump (e.g., due to a change in the rpm of the roller pumps usually used). However, since only the finding of the flow rates involved is necessary for the applications of the present invention, such influences can be detected by suitable measurement sensors.

Direct flow sensors can be provided for this purpose. However, it is also possible to employ relationships between the flow rate and other quantities. For example, correction of the nominal flow rate can be obtained on the basis of rpm by taking into account the boost pressure.

In this way it is possible to obtain very precise a information about the efficiency of a dialyzer or a dialysis treatment without having to interrupt the treatment by too frequent measurements of the clearance and/or dialysance. Such measurements could otherwise result in impairment of the actual dialysis treatment, depending on the measurement method and the frequency of the measurements.

BRIEF DESCRIPTION OF THE DRAWINGS

FIG. 1 shows a schematic diagram of the dialysis machine of the present invention.

DETAILED DESCRIPTION

The dialysis machine has a dialyzer 1 divided by a semipermeable membrane 2 into a blood chamber 3 and a dialysis fluid chamber 4. An arterial blood line 5 connected to the inlet of the blood chamber 3 is also connected to a blood pump 6. Downstream from the blood chamber, a venous blood line 7 leads from the outlet of the blood chamber to the patient.

Fresh dialysis fluid is kept on supply in a dialysis fluid source S. A dialysis fluid inlet line 9 leads from dialysis fluid source 8 to the inlet of dialysis fluid chamber 4 of dialyzer 1, while a dialysis fluid outlet line 10 leads from the outlet of the dialysis fluid chamber to a drain 11. A dialysis fluid pump 12 is connected to dialysis fluid outlet line 10.

A balancing device 27 provided for balancing the fluid flowing into and out of the dialyzer has a balancing chamber with two balancing chamber halves 27a, 27b, the first of which is connected to the dialysis fluid inlet line 9 and the second to the dialysis fluid outlet line 10. An ultrafiltration line 28 branching off upstream from dialysis fluid pump 12 opens into the dialysis fluid outlet line again downstream from the second balancing chamber 27b. An ultrafiltration pump 29 whose delivery rate determines the ultrafiltration rate is connected to the ultrafiltration line 28.

The dialysis machine has a control unit 13 which is connected to blood pump 6, dialysis fluid pump 12, and ultrafiltration pump 29 by control lines 14, 15, and 30, respectively. Control unit 13 establishes a certain delivery rate for blood pump 6, dialysis fluid pump 12 and ultrafiltration pump 29, said rate being preselected by the user and variable during the dialysis treatment.

A conductivity sensor 16 for determining the dialysis fluid inlet concentration Cdi of a given substance in the dialysis fluid upstream from the dialysis fluid chamber is provided. The sensor 16 is arranged in the dialysis fluid inlet line 9 at the inlet of the dialysis fluid chamber 4. A conductivity sensor 17 is arranged in the dialysis fluid outlet line 10 at the outlet of dialysis fluid chamber 4 to measure the dialysis fluid outlet concentration Cdo of the respective substance established in the dialysis fluid downstream from the dialyzer during the dialysis treatment.

The measured values of conductivity sensors 16, 17 are supplied over signal lines 18, 19 to a device 21 which has a computer unit 22 for determining clearance C and/or dialysance D. Computer unit 22 is, for example, a microprocessor of the type known in the art. Via a data line 23 leading to control unit 13, device 21, as part of determining the clearance and the dialysance, detects the delivery rates of blood pump 6, dialysis fluid pump 12, and/or ultrafiltration pump 29, which thereby specify the blood flow rate Qb, dialysis fluid rate Qd, and/or the ultrafiltration rate.

To change the Na concentration of the dialysis fluid upstream from dialyzer 1, another device 24 is also provided. The composition of the dialysis fluid flowing into the dialyzer can be varied with device 24. Device 24 is connected to control unit 13 over a control line 20.

The dialysis machine of the present invention may also have other components such as a drip-chamber, cutoff elements, etc., although they are not shown here for the sake of greater clarity.

The efficiency of the dialyzer 1 can be monitored as follows. For a dialysis fluid rate Qd1, blood flow rate Qb1, and ultrafiltration rate Qf1 preselected at the start of a dialysis treatment, the dialysis fluid inlet and outlet concentrations Cdi1, Cdo1 are measured by conductivity sensors 16, 17. Computer unit 22 controls device 24 in such a way that the Na concentration of the dialysis fluid upstream from the dialyzer is increased, and dialysis fluid inlet and outlet concentrations Cdi2, Cdo2 are again measured by conductivity sensors 16, 17. Then the clearance K1 and/or the dialysance at the predetermined dialysis fluid rate Qd1, blood flow rate Qb1, and ultrafiltration rate Qf1 is calculated in the computer unit 22 according to the following equation:

$$K1 = \left(1 - \frac{Cdo2 - Cdo1}{Cdi2 - Cdi1}\right) \cdot (Qd1 + Qf1) \quad (4)$$

On the assumption that only the dialysis fluid rate, the blood flow rate or the ultrafiltration rate changes during a dialysis treatment, the computer unit 22 first calculates the diffusive component D1 of the clearance or dialysance as follows from the clearance K1 or dialysance thus determined and the predetermined blood flow rate Qb1 or ultrafiltration rate Qf1:

$$D1 = \frac{K1 - Qf1}{1 - Qf1/Qe1} \quad (5)$$

The effective blood flow Qe is calculated from the absolute blood flow Qb corresponding to the delivery rate of the blood pump as follows:

$$Qe = Qb\left(1 - \frac{HCT}{100}\right)Fp \quad (6)$$

where HCT is the hematocrit (%) and Fp is the plasma water fraction.

After determining the diffusive component D1 of the dialysance or clearance, the computer unit 22 calculates the diffusive dialysance $D(Qd(t), Qe(t))$ for any dialysis fluid rates Qd(t), blood flow rates Qe(t), and/or ultrafiltration rates Qf(t) according to the following equations:

$$D(Qd(t), Qe(t)) = Qe(t) \cdot \left(1 - \exp\left(\frac{Qd(t)}{Qd1}\ln\left(1 - \frac{DQecorr}{Qd(t)}\right)\right)\right) \quad (7)$$

where $$DQecorr = Qd1\left(1 - \exp\left(\frac{Qe(t)}{Qe1}\ln\left(1 - \frac{D1}{Qd1}\right)\right)\right) \quad (8)$$

The diffusive dialysance $D(Qd(t), Qe(t))$ is always calculated when there is a change in the dialysis fluid rate or blood flow rate, which correlates with the delivery rate of the dialysis fluid pump 12 or blood pump 6. The computer unit 22 calculates the sum of the diffusive and convective dialysance or clearance $K(Qd(t), Qe(t), Qf(t))$ from the diffusive dialysance $D(Qd(t), Qe(t))$ according to the following equation:

$$K(Qd(t), Qe(t), Qf(t)) = D(Qd(t), Qe(t))\left(1 - \frac{Qf(t)}{Qe(t)}\right) + Qf(t) \quad (9)$$

The clearance or dialysance over time is determined during the dialysis treatment. The effective clearance $K_{eff}$ is calculated from the individual values for the clearance by averaging in the computer unit 22.

If the clearance over time during the dialysis treatment with treatment time T is known, the effective clearance $K_{eff}$ can also be calculated by integration according to the following equation:

$$Keff = \frac{1}{T}\int_0^T K(t)dt \quad (10)$$

Although the values for K(t) may be based on different measured values, it is possible according to the present invention to discontinue measurements for values of t where K(t) can be determined with sufficient accuracy according to equation (9).

The values for the clearance and/or dialysance and the effective values are displayed on a display unit 25 which is connected by a data line 26 to the computer unit 22. Thus, the purification capacity of the dialyzer can be monitored continuously during the dialysis treatment.

What is claimed is:

1. A dialysis machine, comprising:
   a dialyzer;
   a semipermeable membrane dividing the dialyzer into a blood chamber and a dialysis fluid chamber, the blood chamber having an inlet and an outlet, and the dialysis fluid chamber having an inlet and an outlet;
   an arterial blood line connected to the inlet of the blood chamber;
   a venous blood line connected to the outlet of the blood chamber;
   a dialysis fluid inlet line connected to the inlet of the dialysis fluid chamber;
   a dialysis fluid outlet line connected to the outlet of the dialysis fluid chamber;
   a first device for determining at least a first measured or predetermined flow rate and a second measured or predetermined flow rate selected from the group of a blood flow rate Qb through the blood chamber, a dialysis fluid flow rate Qd through the dialysis fluid chamber, and an ultrafiltration rate Qf;
   a computer unit configured to:
      establish at least one of a clearance and a dialysance at the first flow rate; and
      determine the at least one of the clearance and the dialysance at the second flow rate on the basis of the at least one of the clearance and a dialysance established at the first flow rate.

2. The dialysis machine of claim 1, wherein the computer unit calculates a diffusive component D1 of the dialysance or the clearance at the predetermined dialysis fluid flow rate Qd1, the predetermined blood flow rate Qb1, and the predetermined ultrafiltration rate Qf1, from the clearance K1 or the dialysance at the predetermined dialysis fluid flow rate Qd1, the predetermined blood flow rate Qb1, and the predetermined ultrafiltration rate Qf1 according to the following equation:

$$DI = \frac{KI - QfI}{1 - QfI/QeI},$$

wherein an effective blood flow Qe is calculated from the blood flow rate Qb corresponding to a delivery rate of a blood pump according to the following equation:

$$Qe = Qb\left(1 - \frac{HCT}{100}\right)Fp,$$

wherein HCT is the hematocrit (%) and Fp is the plasma water fraction.

3. The dialysis machine of claim 2, wherein the computer unit calculates a diffusive dialysance D(Qd(t), Qe(t)) for any dialysis fluid flow rate Qd(t), blood flow rate Qe(t) and ultrafiltration rate Qf(t), from the clearance K1 or the dialysance at the predetermined dialysis fluid flow rate Qd1, the predetermined blood flow rate Qb1, and the predetermined ultrafiltration rate Qf1 according to the following equations:

$$D(Qd(t), Qe(t)) = Qe(t) \cdot \left(1 - \exp\left(\frac{Qd(t)}{QdI}\ln\left(1 - \frac{DQecorr}{Qd(t)}\right)\right)\right)$$

wherein $$DQecorr = QdI\left(1 - \exp\left(\frac{Qe(t)}{QeI}\ln\left(1 - \frac{DI}{QdI}\right)\right)\right).$$

4. The dialysis machine of claim 3, wherein the computer unit calculates the sum of the diffusive and convective dialysance K(Qd(t), Qe(t), Qf(t)) or the clearance from the diffusive dialysance D(Qd(t), Qe(t)) according to the following equation:

$$K(Qd(t), Qe(t), Qf(t)) = D(Qd(t), Qe(t))\left(1 - \frac{Qf(t)}{Qe(t)}\right) + Qf(t).$$

5. The dialysis machine of claim 1, wherein the first device is configured so that at least one of the clearance and the dialysance can be determined for different times t during a dialysis treatment and effective clearance $K_{\mathit{eff}}$ can be determined by averaging the dialysances or the clearances for different times t during the dialysis treatment.

6. The dialysis machine of claim 1, further comprising:
a blood pump connected to the arterial blood line or the venous blood line;
a dialysis fluid pump connected to the dialysis fluid inlet line or the dialysis fluid outlet line; and
wherein the first device determines a delivery rate of the blood pump or the dialysis fluid pump.

\* \* \* \* \*

UNITED STATES PATENT AND TRADEMARK OFFICE
CERTIFICATE OF CORRECTION

PATENT NO. : 6,860,866 B1
DATED : March 1, 2005
INVENTOR(S) : Graf et al.

It is certified that error appears in the above-identified patent and that said Letters Patent is hereby corrected as shown below:

Title page,
Item [75], Inventors, change "Niedewerrn" to -- Niederwerrn --;

Column 1,
Line 15, change "flow ii rate" to -- flow rate --.

Signed and Sealed this

Twenty-first Day of June, 2005

JON W. DUDAS
*Director of the United States Patent and Trademark Office*